United States Patent [19]

Say et al.

[11] 4,105,704
[45] Aug. 8, 1978

[54] METHOD FOR PREPARING AND USING A SOLUBLE METAL PENTAFLUORIDE-HYDROGEN FLUORIDE CATALYST

[75] Inventors: Geoffrey R. Say; William C. Baird, Jr., both of Baton Rouge, La.

[73] Assignee: Exxon Research & Engineering Co., Linden, N.J.

[21] Appl. No.: 758,054

[22] Filed: Dec. 29, 1976

[51] Int. Cl.² .......................... C07C 3/52; C07C 5/24
[52] U.S. Cl. .......................... 260/666 P; 260/668 A; 260/668 B; 260/669 R; 260/671 A; 260/683.2; 260/683.4 R; 260/683.45; 260/683.47; 260/683.51; 252/411 R; 252/434; 252/441
[58] Field of Search ............... 260/666 P, 671, 668 A, 260/668 B, 683.4, 683.2, 683.65, 669, 683.45, 683.47, 683.51; 252/411 R, 434, 441

[56] References Cited

U.S. PATENT DOCUMENTS

| | | | |
|---|---|---|---|
| 3,830,871 | 8/1974 | Mayer et al. | 260/683.74 |
| 3,852,184 | 12/1974 | Siskin et al. | 260/666 P |
| 3,948,761 | 4/1976 | Siskin et al. | 260/666 P |
| 4,025,577 | 5/1977 | Siskin et al. | 260/683.47 |

Primary Examiner—Veronica O'Keefe
Attorney, Agent, or Firm—John W. Ditsler

[57] ABSTRACT

A soluble HF/TaF$_5$ catalyst is prepared in the absence of an organic solvent according to the steps of:

(1) contacting tantalum metal with substantially anhydrous liquid HF to form soluble TaF$_5$, the amount of HF being sufficient to maintain the TaF$_5$ thus formed as a homogeneous substantially liquid phase catalyst at a temperature ranging from about 0° to 150° C, (2) contacting the catalyst thus formed with a hydrocarbon feedstock in a hydrocarbon conversion process to form an acid catalyst phase and a hydrocarbon product phase, (3) stripping HF from said catalyst phase with a gas containing molecular hydrogen thereby reducing the mole ratio of HF to TaF$_5$, and (4) passing the stripped acid catalyst phase from step (3) to the hydrocarbon conversion process, thereby maintaining the mole ratio of HF to TaF$_5$ within said process at a level between that obtained in step (1) and step (3).

15 Claims, 1 Drawing Figure

U.S. Patent     Aug. 8, 1978     4,105,704
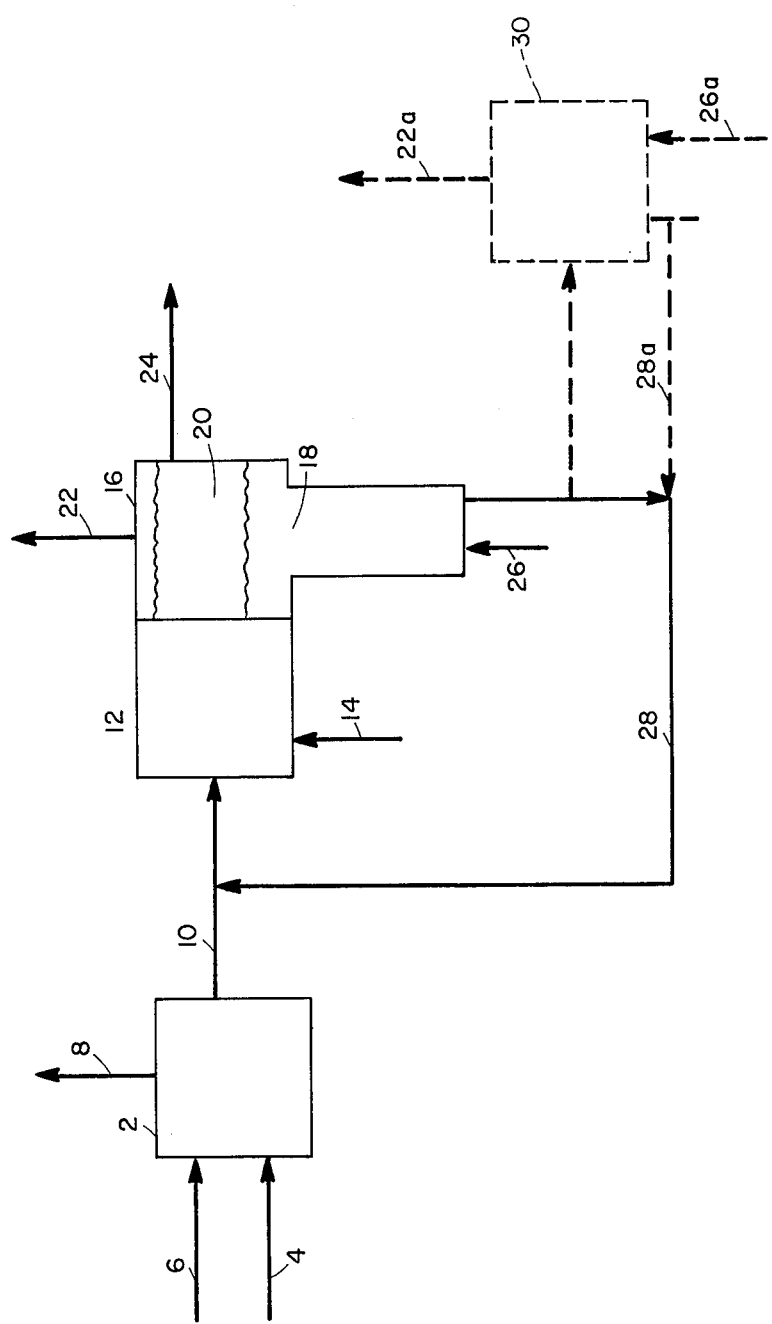

METHOD FOR PREPARING AND USING A SOLUBLE METAL PENTAFLUORIDE-HYDROGEN FLUORIDE CATALYST

BACKGROUND OF THE INVENTION

1. Field of the Invention

The present invention relates to a method for preparing a hydrocarbon conversion catalyst. More particularly, this invention relates to the preparation of a substantially liquid phase hydrocarbon conversion catalyst without the use of an organic solvent.

2. Description of the Prior Art

The liquid phase strong acid catalyst comprising HF and $TaF_5$ is known to be useful in promoting various hydrocarbon conversion reactions (see, for example, U.S. Pat. Nos. 2,683,763; 2,683,764; 3,728,411; 3,852,184; 3,888,937; 3,901,790; 3,948,761, as well as application Ser. No. 586,176, filed June 12, 1975, the disclosures of which are incorporated herein by reference). These reactions include isomerization, alkylation, disproportionation, naphthene cleavage, aromatic hydrogenation, and the like. It is also known that the effectiveness of this catalyst system for such hydrocarbon conversion reactions is related to the molar ratio of hydrogen fluoride to tantalum pentafluoride. More particularly, in order to maximize catalyst activity and activity maintenance, it is desirable to operate these processes at a catalyst composition wherein the molar ratio of HF to $TaF_5$ is at least 1, preferably at least 5, more preferably at least 10 and most preferably within the range of from 5 to 40. However, at such ratios, $TaF_5$ is not completely soluble in HF under the process conditions normally associated with said hydrocarbon conversion processes, such that the catalysts exists as a slurry. This creates operating problems related to homogeneous catalyst transfer, losses of $TaF_5$ via deposition and line plugging. To alleviate this problem, the prior art has suggested the use of an organic solvent to solubilize the catalyst. A very effective solvent is benzene. However, substantial quantities of benzene, i.e. up to 50 mole percent on $TaF_5$, are required. Such amounts of benzene depress catalyst activity and favor the formation of undesirable compounds that tend to adversely affect the ability of the catalyst to effect the hydrocarbon conversion reaction. In addition, about a 35 mole % on $TaF_5$ of naphthenes, e.g. methylcyclopentane, have also been found to be suitable catalyst solubilizers. However, the resultant solution is sensitive to variations in process conditions such that $TaF_5$ will precipitate if temperature and hydrogen partial pressure are not properly controlled. In addition, methylcyclopentane tends to react with components of the feedstock, particularly aromatics, to form catalyst poisons. Thus, it would be desirable to have available a simple and convenient method to solubilize the $HF/TaF_5$ catalyst system without the disadvantages attendant in the prior art processes.

SUMMARY OF THE INVENTION

Now, according to the present invention, a simple and convenient method has been discovered to prepare and transfer a substantially liquid phase $HF/TaF_5$ catalyst to a reaction zone as a dilute solution and then to concentrate the catalyst to the desired composition as the reaction proceeds. This may be effected according to the steps of:

(1) contacting tantalum metal with substantially anhydrous liquid HF to form $TaF_5$, the amount of HF being sufficient to maintain the $TaF_5$ thus formed in a homogeneous substantially liquid phase solution at temperatures ranging from 0° to 150° C, (2) reacting the catalyst thus formed with a hydrocarbon feedstock in a hydrocarbon conversion zone to form an acid catalyst phase and a hydrocarbon product phase, (3) stripping hydrogen fluoride from said catalyst phase formed in step (2) with a gas containing molecular hydrogen, thereby forming an acid catalyst having a reduced mole ratio of HF to $TaF_5$ relative to the catalyst formed in step (1), and (4) passing the acid catalyst formed in step (3) to the hydrocarbon conversion process of step (2) so as to maintain the mole ratio of $HF/TaF_5$ in said process between that of the catalyst formed in steps (1) and (3).

BRIEF DESCRIPTION OF THE DRAWING

The single FIGURE is a diagrammatic representation of one embodiment of the present invention.

DETAILED DESCRIPTION OF THE INVENTION

Having thus described the invention in general terms, reference is now made to the FIGURE which shows one embodiment of the present invention. Such details are included as are necessary for a clear understanding of how the present invention may be employed. No intention is made to unduly limit the scope of the present invention to the particular configuration shown as variations obvious to those having ordinary skill in the art of hydrocarbon conversion reactions and catalyst preparation techniques are included within the broad scope of the present invention.

Referring now to the FIGURE, there is shown a preparation zone 2 into which tantalum metal and substantially anhydrous liquid HF are introduced via lines 4 and 6, respectively, and react as shown in Equation (1) below:

$$Ta + HF \rightarrow TaF_5 + 2.5 H_2 \qquad (1)$$

The hydrogen evolved is shown leaving preparation zone 2 via line 8. The reactants are well-known articles of commerce and may be obtained from various suppliers throughout the chemical industry.

According to this invention, the reactants are contacted at conditions such that there will be formed a homogeneous, substantially liquid phase solution of $HF/TaF_5$. In general, the temperature can range from 0° to 150° C but preferably the temperature will be maintained in the range from about 25° to about 100° C, most preferably from about 25° to about 70° C. This corresponds to $HF/TaF_5$ mole ratios ranging from about 100/1 to 50/1 at which $TaF_5$ will form a substantially homogeneous solution in HF. Since the solubility of $TaF_5$ in HF increases with temperature, the ratio at which a homogeneous solution is formed will decrease as the temperature is increased. In a preferred embodiment, the reactants are contacted at a temperature of 65° C to form the $TaF_5$ and then the $HF/TaF_5$ mole ratio is adjusted to about 50/1 by the addition of additional HF to provide a substantially homogeneous solution at about 50° C. The reactants need be contacted only for a time sufficient to obtain a substantially homogeneous solution at the particular temperature employed. Typically, the solubilization can be effected within 24 hours, and preferably between about 1 and about 20 hours, more preferably between 1 and about 15 hours. Pressures are not critical in the present invention and may range broadly. Typically the pressure will range from about 1 to about 40 atmospheres.

Preparation zone 2 may be any suitable apparatus for effecting the solubilization of the catalyst. The process may be carried out either in a batch or continuous type of operation, although it is preferred for economic reasons to carry out the process continuously. It is desirable that intimate contact between the tantalum and HF be obtained in preparation zone 2. Therefore, conventional mixing means such as mechanical agitators and the like may be employed. If batch operations are employed, the solubilized catalyst may be stored therein for use as needed. In continuous operations, a HF/TaF slurry is introduced into the preparation zone and an HF/TaF$_5$ solution emerges therefrom.

The dilute HF/TaF$_5$ solution thus prepared is then passed via line 10 into hydrocarbon conversion zone 12 and contacted therein with a hydrocarbon feedstock introduced via line 14. A wide variety of hydrocarbon conversion reactions may be effected within said hydrocarbon conversion zone including those that occur under the influence of Friedel-Crafts catalysts, e.g. isomerization, alkylation, polymerization, cracking, hydrogenation, disproportionation and the like. Similarly, the feedstocks employed will be those corresponding to the particular hydrocarbon conversion reaction occurring within zone 12. Typically, the feedstocks used in such processes will contain hydrocarbons containing from about 1 to about 20 carbon atoms and will have a 50 percent boiling point below 450° F, preferably below 400° F, measured at atmospheric pressure. Similarly, the particular temperatures and pressures employed in zone 12 will vary with the reaction being conducted therein. However, temperatures will generally be in the range of from 0° to about 150° C with total pressures ranging from about 1 to about 150 atmospheres. In like manner, molecular hydrogen may or may not be necessary depending upon the requirements of the particular hydrocarbon conversion process. Preferably, however, hydrogen will be present.

After allowing sufficient residence time for the reaction to progress, typically on the order of from about 1 minute to about 1 hour or more, the hydrocarbon-partially deactivated catalyst mixture formed in said hydrocarbon conversion zone 12, often referred to as an "emuslsion mixture," is then passed into settling zone 16. The emulsion mixture will separate in settling zone 16 into a heavier catalyst phase 18 containing the tantalum pentafluoride and HF and a lighter hydrocarbon phase 20 containing hydrocarbon product along with smaller amounts of tantalum pentafluoride and hydrogen fluoride which are dispersed and/or dissolved in said hydrocarbon product. Any gases present in the system at this point, e.g. hydrogen, will disengage and pass from the settler via line 22.

As shown in the FIGURE, the hydrocarbon product is removed from the system via line 24 and may undergo further processing (for example to remove the tantalum pentafluoride according to the method disclosed in U.S. Pat. No. 3,830,871, the disclosures of which are incorporated herein by reference) or be sent to storage.

In the embodiment shown in the drawing, the catalyst is concentrated in the settler by stripping HF therefrom using a gaseous stream containing molecular hydrogen which is introduced via line 26. Thus, the mole ratio of the HF to TaF$_5$ of the catalyst stream leaving settling zone 16 via line 28 is less than the HF/TaF$_5$ mole ratio of the catalyst stream 10 entering hydrocarbon conversion zone 12. The solubility of the TaF$_5$ in HF is retained during the stripping operation due to the presence in the catalyst of various ionic species, e.g. ions such as $Ta_2F_{11}{}^-$, $Ta_3F_{16}{}^-$ and the like, that are formed during contact of the TaF$_5$/HF and the hydrocarbon in zone 12. The formation of these ions serves to maintain the TaF$_5$ in solution such that the HF/TaF$_5$ catalyst can be concentrated by HF removal while still maintaining a homogeneous, i.e. non-slurried, solution. The catalyst phase withdrawn from zone 16 may then be recycled to the hydrocarbon conversion process directly or, if desired, be combined with the fresh catalyst stream 10 such that the mole ratio of HF to TaF$_5$ is now less than the previous value of stream 10.

This process continues in this manner until the desired catalyst inventory in conversion zone 12 has been achieved. At this point, the stripping of catalyst phase 18 continues until the mole ratio of HF/TaF$_5$ desired for the particular hydrocarbon conversion process is obtained. As the catalyst phase 18 is concentrated, the activity of the catalyst in hydrocarbon conversion zone 12 increases so as to maintain an adequate supply of ionic species which, in turn, solubilize additional TaF$_5$ as described above, thereby maintaining the solubility of same. Thus, the present invention carefully balances HF removal with hydrocarbon conversion activity so as to afford substantially complete solubility of the catalyst throughout the entire hydrocarbon conversion process.

If desired, the catalyst phase 18 can be stripped with hydrogen in a separate vessel 30 by contact with hydrogen introduced via line 26a. The HF thus removed and the hydrogen are shown leaving vessel 30 via line 22a. This method has the advantage of providing catalyst holdup or on-line storage if desired.

As noted above, the present invention is applicable to a wide variety of reactions that occur under the influence of Friedel-Crafts catalysts. It is, however, particularly applicable to isomerization and alkylation reactions. Typical isomerizable feedstocks include acyclic and alicyclic aliphatic hydrocarbons having at least four carbon atoms that are converted to a product enriched in an isomer thereof. Typically, acyclic hydrocarbons having at least four carbon atoms, that is straight chain or branched chain paraffins having from about 4 to 20 carbon atoms, preferably from about 4 to 12 carbon atoms, are converted to branched materials having higher octane ratings. Additionally, alicyclic hydrocarbons (naphthenes) having at least 6 carbon atoms, typically from 6 to about 20 carbon atoms, preferably 6 to 15 carbon atoms, can be converted to isomers thereof by contacting the same with hydrogen in the presence of the catalyst system described previously. Mixtures of acylic and alicyclic hydrocarbons can be used as the process feedstock. In a typical commercial operation, a paraffin stream containing mixtures of various types of open chain and closed chain paraffins is used as the process feedstock. Typical isomerization reaction conditions are summarized below.

| Range | Suitable | Preferred |
|---|---|---|
| Temperature, ° C | 0–150 | 30–75 |
| Hydrogen Partial | | |

-continued

| Range | Suitable | Preferred |
| --- | --- | --- |
| Pressure, atm. | 0.1–140 | 0.3–25 |
| Reaction Time, min | 0.5–1500 | 1–500 |
| Moles $H_2$/Mole Hydrocarbon | 0.01–2.5 | 0.1–1.0 |
| Space Velocity V/Hr./V | 0.05–200 | 0.25–50 |

In the alkylation of hydrocarbons with olefins, suitable olefinic starting materials are ethylene, propylene, butylenes, trimethyl ethylene and other isomeric pentenes, and similar higher monoolefinic hydrocarbons of either a straight chain or branched chain structure. Olefins containing 2 to about 12 carbon atoms per molecule are preferred while olefins containing 2 to 5 carbon atoms per molecule are particularly preferred. The reaction mixtures may also contain some amounts of diolefins. Although it is desirable from an economic viewpoint to use the normally gaseous olefins as reactants, normally liquid olefins may also be used. Thus, polymers, copolymers, interpolymers, crosspolymers, etc., of the above-mentioned olefins, as for example, propylene dimer, the diisobutylene and triisobutylene polymers, the codimer of normal and isobutylenes and the like may be used. The use of mixtures of two or more of the above-described olefins is also envisioned for this purpose.

Hydrocarbon feedstocks that are suitable for use in alkylation processes include paraffins, aromatic alkyl substituted aromatic hydrocarbons and mixtures thereof. The paraffins as herein defined include the acyclic and alicyclic hydrocarbons. The acyclic hydrocarbons (straight and branched chain materials) contain at least 1, preferably 1 to about 12 carbon atoms per molecule, and may be exemplified by methane, ethane, propane, butanes, methylbutanes, n-pentane, methylpentanes, methylhexanes, and the like. The alicyclic hydrocarbon (naphthenes) contain at least 5, typically from 5 to about 15 carbon atoms per molecule, preferably 6 to 12 carbon atoms and may be exemplified by methylcyclopentane, dimethylcyclopentane, methylcyclohexane, ethylcyclohexane, n-pentylcyclohexane and the like. Useful aromatic and alkyl aromatic hydrocarbons contain at least 6, preferably 6 to about 20 carbon atoms per molecule and are exemplified by benzene, ethyl benzene, n-butyl benzene and the like. Other acyclic or alicyclic hydrocarbons commonly found in conventional petroleum hydrocarbon light naphtha streams and the like may be present. Typical alkylation reaction conditions are summarized below:

| Range | Suitable | Preferred |
| --- | --- | --- |
| Temperature, °C | −100–+150 | −10–+80 |
| Hydrogen Partial Pressure, atm. | 0.1–100 | 0.3–25 |
| Reaction Time, min. | 0.001–60+ | 0.001–45 |
| Space Velocity based on olefin, V/Hr./V | 0.01–10 | 0.04–5 |

A paraffin can also be alkylated with another another paraffin using the catalyst system described herein. For example, a paraffinic feedstock comprising a member selected from the group consisting of $iC_4$–$C_6$ acyclic hydrocarbons, $C_5$–$C_{15}$ alicyclic hydrocarbons and mixtures thereof can be alkylated with larger paraffins, i.e. paraffins or a mixture of paraffins having more than 6 carbon atoms, to form lower molecular weight materials. More specifically, a paraffinic feedstock containing smaller paraffins, i.e. isobutane, isopentanes, isohexanes or mixtures thereof, can undergo alkylation with larger paraffins to form lower molecular weight hydrocarbons. Thus, isobutane can undergo a paraffin alkylation reaction with a heptane to form pentanes and hexanes. The conditions employed are the same as those shown in the preceding table. However, hydrogen may or may not be present. It is preferred that all of the above-mentioned hydrocarbon conversion processes be conducted under substantially anhydrous conditions.

The following examples are presented to further illustrate the process of the present invention and are not intended to unduly restrict the limits of the claims appended hereto:

EXAMPLE 1

Solubilization of Catalysts Using Organic Solvent

Into a Hastelloy C catalyst preparation vessel of 22 U.S. gallon capacity (having a mixer and external heating coil) were charged 58.2 pounds of tantalum metal powder 0.34 pound moles) and 97 pounds (4.85 pound moles) of anhydrous hydrofluoric acid. The reaction was heated and stirred at 165°–185° F until the calculated volume of hydrogen was produced as measured by a wet test meter. The slurry of tantalum pentafluoride in hydrogen fluoride (composition corresponding to 10 moles of HF per 1 mole of $TaF_5$) was cooled to ambient temperature. The tantalum pentafluoride was brought into solution by the addition of 12.6 pounds of benzene. The resultant clear catalyst solution was subsequently transferred to an isomerization reactor through which a hexane feed containing 2.5 weight % benzene was circulating continuously. The activity declined by a factor of 6 over 50 hours of operation from an initial rate constant of 6 hours$^{-1}$. The catalyst composition was maintained at 8–12/1 HF/$TaF_5$ over this interval. The results from this experiment are summarized in the table below.

EXAMPLE 2

Solubilization of Catalyst Without Organic Solvent

Into a catalyst preparation vessel were charged 21.4 pounds (0.118 pound moles) of powdered tantalum and 130.1 pounds (6.5 pound moles) of anhydrous HF. The reactants were mixed at 165°–185° F to give a soluble catalyst of 50/1 HF/$TaF_5$ molar ratio. The homogeneous catalyst was added to a reactor through which hexane feed containing 250 wppm benzene was flowing continuously. Over a period of 100 hours, the catalyst was concentrated to a 40/1 composition. The tantalum pentafluoride remained soluble at all times. Activity was constant at a rate constant of 10–11 hours$^{-1}$ over this interval. The results from this experiment are also summarized in the table below.

| Example No. | 1 | 2 |
| --- | --- | --- |
| HF/$TaF_5$ mole ratio, initial | 10/1 | 50/1 |
| Solubilizing agent | Benzene | None |
| Catalyst/Oil, V/V | | 1/1 |
| Feedrate, gal/hr. | | 5.0 |
| Temperature, °F. | | 122 |
| Pressure, psig | | 100 |
| Time, hr. | 50 | 100 |
| HF/$TaF_5$ mole ratio, final | 8–12/1 | 40/1 |
| k, hr$^{-1}$ initial | 6 | 10.5 |
| k, hr$^{-1}$ final | 1 | 11 |

The above results illustrate that while benzene is capable of providing a soluble catalyst, it has an adverse effect on the catalyst activity. Example 2 shows that a soluble, active catalyst can be prepared and employed without the attendant disadvantages associated with the use of organic solvents.

Although the above discussion has been directed to forming a catalyst comprising tantalum pentafluoride and HF, it should be clearly understood that the above process is equally applicable, in all respects, to forming a catalyst comprising niobium pentafluoride and HF. Thus, the invention will apply to preparing a homogeneous substantially liquid phase catalyst which comprises a metal pentafluoride selected from the group consisting of tantalum pentafluoride, niobium pentafluoride and mixtures thereof and hydrogen fluoride. The preferred metal pentafluoride is tantalum pentafluoride.

What is claimed is:

1. A process for preparing and using a homogeneous liquid phase catalyst containing a metal pentafluoride selected from the group consisting of tantalum pentafluoride, niobium pentafluoride and mixtures thereof and hydrogen fluoride, the mole ratio of HF to metal pentafluoride being between 5 and 40, which comprises the steps of
   (1) contacting tantalum metal, niobium metal or mixtures thereof with substantially anhydrous liquid HF at a temperature ranging from 0° to 105° C for a time sufficient to form a homogeneous liquid phase catalyst having a mole ratio of HF to metal pentafluoride between about 100/1 to 50/1, said contacting being effected in the absence of an organic solvent,
   (2) contacting the catalyst formed in step (1) with a hydrocarbon feedstock in a hydrocarbon conversion process, thereby forming an acid catalyst phase and a hydrocarbon product phase,
   (3) stripping HF from the acid catalyst phase formed in step (2) with a gas containing molecular hydrogen, thereby forming a homogeneous liquid phase acid catalyst having a mole ratio of HF to metal pentafluoride less than that of the acid catalyst formed in step (1), and
   (4) passing the acid catalyst formed in step (3) to the hydrocarbon conversion process of step (2) until a homogeneous liquid phase catalyst having a mole ratio of HF to metal pentafluoride between 5 and 40 is obtained.

2. The process of claim 1 wherein the temperature in step (1) ranges from about 25° to about 70° C.

3. The process of claim 1 wherein said hydrocarbon conversion is effected in the presence of hydrogen.

4. The process of claim 3 wherein said hydrocarbon conversion process is isomerization and said hydrocarbon feedstock comprises an acyclic hydrocarbon having at least four carbon atoms, an alicyclic hydrocarbon having at least six carbon atoms and mixtures thereof.

5. The process of claim 3 wherein said hydrocarbon conversion process is alkylation and said hydrocarbon feedstock comprises an acyclic hydrocarbon having at least one carbon atom, an alicyclic paraffin having at least 5 carbon atoms, an aromatic and alkylaromatic hydrocarbon having at least 6 carbon atoms or mixtures thereof and said hydrocarbon feedstock is reacted with olefins containing from 2 to about 12 carbon atoms per molecule.

6. The process of claim 1 wherein said hydrocarbon conversion process is alkylation and said hydrocarbon feedstock comprises an acyclic hydrocarbon having at least one carbon atom, an alicyclic paraffin having at least 5 carbon atoms, an aromatic and alkylaromatic hydrocarbon having at least 6 carbon atoms or mixtures thereof and said hydrocarbon feedstock is reacted with olefins containing from 2 to about 12 carbon atoms per molecule.

7. The process of claim 1 wherein the mole ratio of HF to metal pentafluoride in said hydrocarbon conversion process after passing the acid catalyst formed in step (3) to said process is at least 10:1.

8. The process of claim 1 wherein said hydrocarbon conversion process is alkylation and wherein a hydrocarbon feedstock comprising a member selected from the group consisting of $iC_4$–$C_6$ acyclic hydrocarbons, $C_5$–$C_{15}$ alicylic paraffins and mixtures thereof is alkylated with a paraffin having more than 6 carbon atoms.

9. The process of claim 1 wherein said process is conducted under substantially anhydrous conditions.

10. The process of claim 1 wherein the metal pentafluoride is tantalum pentafluoride.

11. A process for maintaining the mole ratio of HF to metal pentafluoride between 5 and 40 in a homogeneous liquid phase catalyst comprising a metal pentafluoride selected from the group consisting of tantalum pentafluoride, niobium pentafluoride and mixtures thereof and hydrogen fluoride, which comprises the steps of
   (1) contacting tantalum metal, niobium metal or mixtures thereof with substantially anhydrous liquid HF at a temperature ranging from 0° to 150° C for a time sufficient to form a homogeneous liquid base catalyst having a mole ratio of HF to metal pentafluoride between from about 100/1 to 50/1, said contacting being effected in the absence of an organic solvent,
   (2) contacting the catalyst formed in step (1) with a hydrocarbon feedstock in a hydrocarbon conversion process, thereby forming an acid catalyst phase and a hydrocarbon product phase,
   (3) stripping HF from the acid catalyst phase formed in step (2) with a gas containing molecular hydrogen, thereby forming a homogeneous liquid phase acid catalyst having a mole ratio of HF to metal pentafluoride less than that of the catalyst formed in step (1), and
   (4) passing the acid catalyst formed in step (3) to the hydrocarbon conversion process of step (2) so as to maintain the mole ratio of HF to metal pentafluoride between 5 and 40.

12. The process of claim 11 wherein said hydrocarbon conversion process is alkylation and said hydrocarbon feedstock comprises an acyclic hydrocarbon having at least one carbon atom, an alicyclic paraffin having at least 5 carbon atoms, an aromatic and alkylaromatic hydrocarbon having at least 6 carbon atoms or mixtures thereof and said hydrocarbon feedstock is reacted with olefins containing from 2 to about 12 carbon atoms per molecule.

13. The process of claim 11 wherein said hydrocarbon conversion is effected in the presence of hydrogen.

14. The process of claim 13 wherein said hydrocarbon conversion process is isomerization and said hydrocarbon feedstock comprises an acyclic hydrocarbon having at least four carbon atoms, an alicyclic hydrocarbon having at least six carbon atoms and mixtures thereof.

15. The process of claim 11 wherein the metal pentafluoride is tantalum pentafluoride.

* * * * *

UNITED STATES PATENT OFFICE
CERTIFICATE OF CORRECTION

Patent No. 4,105,704                    Dated August 8, 1978

Inventor(s) Geoffrey R. Say and William C. Baird, Jr.

It is certified that error appears in the above-identified patent and that said Letters Patent are hereby corrected as shown below:

At column 7, line 28, delete "105°C" and insert in place thereof -- 150°C --.

Signed and Sealed this

Third Day of April 1979

[SEAL]

Attest:

RUTH C. MASON
Attesting Officer

DONALD W. BANNER
Commissioner of Patents and Trademarks